United States Patent [19]

Kobayashi et al.

[11] Patent Number: 4,996,067

[45] Date of Patent: Feb. 26, 1991

[54] FEED ADDITIVE FOR RUMINANTS

[75] Inventors: Takaaki Kobayashi, Yokohama; Takahumi Tosa, Kawasaki; Hiroyuki Sato, Yokohama; Hiroyoshi Okada, Machida; Masao Miyake; Kenji Mori, both of Yokohama, all of Japan

[73] Assignees: Mitsubishi Kasei Corporation; Ajinomoto Co., Inc., both of Tokyo, Japan

[21] Appl. No.: 381,837

[22] Filed: Jul. 19, 1989

[30] Foreign Application Priority Data

Jul. 19, 1988 [JP] Japan ................... 63-178256
Jul. 19, 1988 [JP] Japan ................... 63-178257
Jul. 19, 1988 [JP] Japan ................... 63-178258

[51] Int. Cl.$^5$ ............................... A23D 1/00
[52] U.S. Cl. ............................. 426/96; 426/72; 426/74; 426/303; 426/310; 426/656; 426/807; 424/428
[58] Field of Search ............. 426/96, 89, 302, 303, 426/310, 656, 453–456, 807, 72, 74; 424/482, 489, 428

[56] References Cited

U.S. PATENT DOCUMENTS

| | | | |
|---|---|---|---|
| 4,508,741 | 4/1985 | Corbett et al. | 426/303 |
| 4,717,567 | 1/1988 | Wu et al. | 424/462 |
| 4,832,967 | 5/1989 | Autant et al. | 426/303 |

*Primary Examiner*—R. B. Penland
*Attorney, Agent, or Firm*—Oblon, Spivak, McClelland, Maier & Neustadt

[57] ABSTRACT

A feed additive for ruminants, which comprises cores containing an acid salt of a basic amino acid, and a first coating layer and a second coating layer coated sequentially on the surface of each core, wherein said first coating layer contains at least one first coating agent selected from the group consisting of a neutral or weakly acidic organic substance, a substantially neutral fine powder of inorganic substance, a non-ionic hydrophilic polymer substance and an anionic hydrophilic polymer substance and being physiologically acceptable to the ruminants, and the second coating layer contains as a second coating agent a polymer soluble or swellable in water in an acidic region of a pH of at most 5.5.

21 Claims, No Drawings

FEED ADDITIVE FOR RUMINANTS

The present invention relates to a feed additive for ruminants. More particularly, it relates to a feed additive for ruminants wherein a biologically active substance in the feed additive is protected so that it will not be decomposed in the rumen of the ruminant, and it will be digested and absorbed in the abomasum or subsequent digestive tract at high efficiency.

It is common to incorporate a small amount of a feed additive to a feed for the purpose of supplementing the nutrients for livestock, or preventing or controlling diseases. In the case of ruminants, orally administered amino acids, proteins and other biologically active substances will, in their substantial parts, be decomposed to ammonia or carbon dioxide gas by fermentation by microorganisms in the weakly acidic to weakly alkaline rumen. Bacteria and protozoa in the rumen utilize ammonia for their growth and proliferation, and proteins of microorganisms formed by the proliferation will be sent to the strongly acidic abomasum which corresponds to the stomach of a single stomach animal and partially digested and absorbed there. This process will be completed in the small intestine, and the digested feed is absorbed there. Thus, the absorption efficiency is low.

Heretofore, it has been proposed to coat the biologically active substances with various coating substances in order to let the biologically active substances pass through the rumen without being decomposed by microorganisms and to let them efficiently be absorbed in the abomasum or subsequent digestive tract. However, no adequate effect has yet been obtained.

For example, Japanese Examined Patent Publication No. 41203/1987 proposes to coat cores made of L-lysin hydrochloride, with a polymer substance such as cellulose propionate morpholinobutyrate or poly(vinylpyridine) which is durable in the environment of the rumen, but is soluble or swellable in the strongly acidic abomasum. However, L-lysine hydrochloride is highly soluble in water, and its solution is acidic. Accordingly, with a coating agent highly sensitive to an acid as mentioned above, it is extremely difficult to prevent the elution in the environment of the rumen. Therefore, the core material is preliminarily mixed or coated with a basic inorganic substance such as basic magnesium carbonate or magnesium hydroxide for neutralization to a level of pH 5.5 or higher.

However, such a basic substance serves to neutralize the acid in the stomach when the core material is eluted in the abomasum, and it is feared that the pH of the gastric fluid tends to be high, unless such is desired. The specific gravity of the particles of the feed additive is desired to be close to the specific gravity of the gastric fluid so that the retention time in the rumen can be maintained at a proper level. However, when a basic inorganic substance is used in combination, the specific gravity of the particles increases, and the retention time in the rumen tends to be long, whereby the elution of the particles in the rumen is likely to result.

Further, the lysin used as the core material is highly hygroscopic by itself and tends to absorb carbon dioxide from air and be decomposed while generating a very bad odor (as disclosed in Japanese Unexamined Patent Publication No. 91850/1984). In a case where a basic substance is used in combination with an acid salt of a basic amino acid such as lysin hydrochloride, if water is employed in the granulating step, the granulated particles are likely to have a slightly yellow color, or they tend to generate an odor when left to stand still in a humidified state. The reason is not clearly understood. However, it is highly likely that an acid such as hydrochloric acid neutralizing the basic amino acid is partially neutralized in the presence of the moisture to form a free basic amino acid, which is then likely to be decomposed by microorganisms, thus leading to a property change.

The present invention provides a feed additive for ruminants, which comprises cores containing an acid salt of a basic amino acid, and a first coating layer and a second coating layer coated sequentially on the surface of each core, wherein said first coating layer contains at least one first coating agent selected from the group consisting of a neutral or weakly acidic organic substance, a substantially neutral fine powder of inorganic substance, a non-ionic hydrophilic polymer substance and an anionic hydrophilic polymer substance and being physiologically acceptable to the ruminants, and the second coating layer contains as a second coating agent a polymer soluble or swellable in water in an acidic region of a pH of at most 5.5.

The feed additive of the present invention is excellent in the protection of the core material in the rumen of a ruminant and in the release thereof in the abomasum. Further, it contains no basic substance, whereby the property change of the acid salt of a basic amino acid such as lysin hydrochloride can be avoided. Now, the present invention will be described in detail with reference to the preferred embodiments.

CORE MATERIAL

In the feed additive for ruminants according to the present invention, an acid salt of a basic amino acid being a biologically active substance or a mixture thereof with other biologically active substance is used as the core material.

The acid salt of a basic amino acid may be at least one member selected from the group consisting of acid salts such as hydrochlorides, phosphates, nitrates and acetates, of basic amino acids such as lysine, arginine, histidine, hydroxylysine and ornithine.

Said other biologically active substance to be used in combination with the acid salt of a basic amino acid, includes nutrients, feeds containing nutrients, or medicines. Preferably, it is at least one member selected from the group consisting of neutral amino acids, amino acid derivatives, hydroxy homologues of amino acids, proteins, hydrocarbons, vitamins and veterinary medicines. Specifically, it includes neutral amino acids such as methionine, leucine, isoleucine, valine, cysteine, tryptophan, threonine and phenylalanine; amino acid derivatives such as N-acylamino acid and N-hydroxymethyl methionine.calcium salt; hydroxy homologues of amino acids such as 2-hydroxy-4-methylmercapto butyric acid and its salts; natural nutrient powders such as grain powder, feather powder and fish powder; proteins such as casein, corn protein and potato protein; carbohydrates such as starch, cane sugar and glucose; vitamins and substances having similar functions, such as vitamin A, vitamin A acetate, vitamin A palmitate, vitamins of group B, thiamine, thiamine hydrochloride, riboflavin, nicotinic acid, nicotinic acid amide, calcium pantothenate, choline pantothenate, pyridoxine hydrochloride, choline chloride, cyano cobalamine, biotin, folic acid, p-aminobenzoic acid, vitamin $D_2$, vitamin $D_3$, $\beta$-carotene and vitamin E; antibiotics such as tetracycline antibiotics, amino glycoside antibiotics, macrolide antibiotics and polyether antibiotics; insecticides such as negfon; vermicides such as piperazine; and hormones such as estrogen, stilbestrol, hexestrol, tyroprotein and goitrogen.

GRANULATION OF THE CORE MATERIAL

Prior to the coating treatment for the first coating layer, the above-mentioned core material is granulated by a conventional granulating method such as extrusion granulation, fluidized granulation, rolling granulation or agitation granulation. For such granulation, it is advantageous to use a binder for granulation, an excipient, a disintegrator or a filler for controlling the specific gravity, as a feed adjuvant which is physiologically acceptable to ruminants.

The binder may be, for example, polyvinylpyrrolidone, hydroxypropylcellulose, polyvinyl alcohol, gum arabic, guaiac gum, sodium arginate, sodium cellulose glycolate and sodium polyacrylate. As the excipient, lactose or mannitol may, for example, be used. Such a binder or excipient is used usually in an amount of from 1 to 50 parts by weight per 100 parts by weight of the core material, and it is usually sprayed in the form of a solution in water and/or an alcohol. The disintegrator includes, for example, a potato starch, corn starch, calcium carboxymethyl cellulose, sodium carboxymethyl cellulose and crystalline cellulose.

As the filler, fine hollow sodium silicate balls, fine hollow sodium borosilicate balls, fine hollow calcium silicate balls or silas balloons may be mentioned as a filler having a specific gravity of less than 1.0, and inorganic substances such as talc, kaolin, mica, silica, calcium silicate and diatomaceous earth may be mentioned as a filler having specific gravity of higher than 2.0. It is preferred to use proper amounts of both substances having a specific gravity of less than 1.0 and a specific gravity of higher than 2.0 so that the specific gravity of the final granulated product will be close to the specific gravity of the gastric fluid of the rumen, whereby it is possible to prevent that the retention time of the feed additive in the stomach is prolonged. Further, conventional additives including binders, excipients, disintegrators, lubricants, colorants, taste regulating agents and odor regulating agents, as disclosed in Drug Formulation Method (A), Fundamentals for Developing Pharmaceutical Products XI, p. 133-154, published by Chijin Shokan, may be used as the case requires.

The core material preferably comprises from 20 to 95% by weight of the acid salt of a basic amino acid, from 0 to 80% by weight of a biologically active substance other than the acid salt of a basic amino acid and from 2 to 50% by weight of a feed adjuvant, based on the total weight of the core material.

FIRST COATING LAYER

In the present invention, the surface of the core material granulated as described above, is first coated with at least one substance selected from the group consisting of a neutral or weakly acidic organic substance, a substantially neutral fine powder of inorganic substance, a non-ionic hydrophilic polymer substance and an anionic hydrophilic polymer substance and being physiologically acceptable to the ruminants. By this first coating layer, the acid salt of a basic amino acid constituting the core material which is highly soluble in water and the aqueous solution of which is acidic, is separated from the second coating layer made of a polymer substance which is soluble or swellable in water in an acidic region of pH 5.5 or less, as described hereinafter, whereby it is possible to attain the excellent protection of the core material in the rumen and the release of the core material in the abomasum without necessity to mix the core material with a known basic substance or to coat the core material with a basic substance.

Preferred examples of the neutral or weakly acidic organic substance to be used as the first coating agent acceptable to the ruminants, are neutral or weakly acidic feeds, foods and feed adjuvants.

For example, it is at least one biologically active substance selected from the group consisting of neutral or weakly acidic amino acids, natural nutrients, proteins and carbohydrates as shown in the following (1) to (4). Particularly preferred is the one which has a solubility of at most 20 g per 100 g of water at 20° C. If the solubility is too high, the protection in the rumen tends to be low.

(1) Neutral amino acids such as methionine, leucine, isoleucine, valine, cysteine, tryptophan, threonine and phenylalanine.
(2) Natural nutrients such as grain powder, feather powder and fish powder.
(3) Proteins such as casein, corn protein and potato protein.
(4) Carbohydrates such as starch, cane sugar and glucose.

Among these substances, amino acids mentioned in item (1) are practically preferred. It is particularly preferred to use one or more selected from methionine, leucine, isoleucine and tryptophan.

Together with the above-mentioned coating agent component, one or more inorganic substances mentioned as fillers for granulation of the core material, may be used in combination.

When such an organic substance is coated on the core material, various supplementary additives used for the granulation of the core material as mentioned above, may be used to form the first coating layer, as the case requires.

The first coating agent is used preferably in an amount of at least 2 parts by weight per 100 parts by weight of the core material. There is no particular upper limit. However, the amount is usually preferably from 3 to 300 parts by weight. If the amount of the first coating agent is too small, no adequate effect for the protection of the core material in the rumen by the first coating layer, is obtainable.

Such a neutral or weakly acidic first coating agent provides the following advantages. Namely, the acid salt of a basic amino acid used as the core material exhibits acidity when dissolved in water and is extremely readily soluble, whereby it is difficult to protect the core material during the retention in the rumen for a long period of time by the coating composed solely of the second coating layer. By the presence of the neutral or weakly acidic first coating substance, the direct contact of the core material and the protective polymer i.e. the second coating layer can be prevented, whereby the protection of the core material in the rumen is improved, and yet the disintegratability in the abomasum is not impaired.

As the physiologically acceptable inorganic substance used as the first coating agent, fine powders of e.g. talc, silica, aluminum, muscovite, phlogopite, bentonite, calcium silicate, kaolin, diatomaceous earth, magnesium silcate and aluminum silicate, may be mentioned. These powders may be used alone or in combination as a mixture of two or more. The particle size of such powders is selected usually within a range of from 0.01 to 300 μm, preferably from 0.1 to 200 μm. Among the above inorganic substances, it is preferred to use at least one member selected from the group consisting of talc, silica, kaolin, magnesium silicate and aluminum silicate. When the first coating layer is formed by using such inorganic substances, the above-mentioned various supplementary additives useful for the granulation of the core material may be employed for the formation of the first coating layer, as the case requires.

The first coating agent is used preferably in an amount of at least 2 parts by weight per 100 parts by weight of the core material. There is no particular upper limit. However, the amount is usualy from 2 to 200 parts by weight, preferably from 3 to 80 parts by weight, per 100 parts by weight of the core material. If the amount of the first coating material is too small, no adequate effect for the protection of the core material will be obtained. On the other hand, if the amount is excessive, the specific gravity of the particles tends to be too high, whereby the retention time in the rumen tends to be long, and efficient utilization of the biologically active substance of the core material will be impossible.

When the neutral or weakly acidic organic substance and/or the fine powder of inorganic substance is used as the first coating agent, any one of conventional coating methods including a pan coating method, a fluidized coating method and a centrifugal fluidized coating method, may be employed for forming the first coating layer. For example, by using a centrifugal fluidized granulation coating apparatus, the granulated core material is supplied together with the first coating agent and an aqueous binder solution in predetermined proportions for coating treatment, followed by drying.

The nonionic hydrophilic polymer substance and the anionic hydrophilic polymer substance to be used as the first coating agent, include the following.

NONIONIC HYDROPHILIC POLYMER SUBSTANCE (1) A synthetic polymer substance including a homopolymer of e.g. vinylpyrrolidone, hydroxyethyl methacrylate, hydroxyethyl acrylate, acrylamide, N-substituted acrylamide, methacrylamide or N-substituted methacrylamide; a copolymer of such a compound with styrene, acrylonitrile, an acrylate, a methacrylate or maleic anhydride; a homopolymer of ethylene oxide or propylene oxide, or a copolymer of both; and a partial hydrolyzate (from 10 to 98 mol%) of a homopolymer of vinyl acetate or a partial hydrolyzate (from 10 to 98 mol%) of a copolymer of vinyl acetate with N-substituted methacrylamide or vinylpyrrolidone, having a molecular weight of from 2,000 to 1,000,000, preferably from 3,000 to 500,000;

(2) A natural polysaccharide selected from the group consisting of guaiac gum, xanthane gum, starch, mannan, galactan, funori, tragacanth gum, dextran, levan and gum arabic;

(3) A semi synthetic polymer substance including a cellulose ether such as hydroxypropyl cellulose, hydroxyethyl cellulose, methyl cellulose, ethyl cellulose, hydroxypropylmethyl cellulose or ethylhydroxyethyl cellulose; a cellulose ester such as cellulose acetate; and viscose and dialdehyde starch.

ANIONIC HYDROPHILIC POLYMER SUBSTANCE (1) A synthetic polymer substance including a homopolymer of acrylic acid or methacrylic acid; a copolymer of acrylic acid or methacrylic acid with styrene, acrylonitrile, an acrylate, a methacrylate or maleic anhydride; a salt of a partial hydrolyzate (from 10 to 98 mol%) of a homopolymer of e.g. acrylamide, acrylonitrile, an acrylate or methacrylate, having a molecular weight of from 2,000 to 1,000,000, preferably from 3,000 to 500,000; and a salt of a partial hydrolyzate (from 10 to 98 mol%) of a copolymer of acrylamide, acrylonitrile, an acrylate or a methacrylate with styrene, hydroxyethyl acrylate or vinyl acetate, having a molecular weight of from 2,000 to 1,000,000, preferably from 3,000 to 500,000;

(2) A semi-synthetic polymer substance including a cellulose ether such as a salt of carboxymethyl cellulose or a salt of carboxymethylethyl cellulose; and a cellulose ester such as a salt of cellulose phthalate or a salt of cellulose acetate phthalate.

The anionic hydrophilic polymer substance is used preferably as an alkali metal salt, an alkaline earth metal salt or an ammonium salt. Particularly preferred is a sodium salt, a potassium salt, a magnesium salt, a calcium salt or an ammonium salt.

To form the first coating layer by means of such polymer substance, it is preferred to employ a nonionic hydrophilic polymer substance.

A physiologically acceptable inorganic substance may be used in combination with such a nonionic hydrophilic polymer substance and/or an anionic hydrophilic polymer substance, for the purpose of adjusting the specific gravity of the particles, controlling the smoothness of the surface of the particles or improving the fixing property of the second coating layer. As the acceptable inorganic substance, talc, aluminum, mica, silica, calcium silicate, kaolin, bentonite, diatomaceous earth, fine hollow glass balls, silas balloons or calcium silicate balloons, may be mentioned. These substances may be used alone or in combination as a mixture of two or more. In this case, various supplementary additives may be employed.

Such a first coating agent is used usually in an amount of at least 5 parts by weight, preferably at least 10 parts by weight, per 100 parts by weight of the core material. There is no particular upper limit. Usually, however, the amount is within a range of from 5 to 300 parts by weight per 100 parts by weight of the core material. If the amount of the first coating agent is too small, the acidic salt of a basic amino acid is soluble in water and exhibits acidity, whereby no adequate effect of the first coating layer will be obtained.

For forming such a first coating layer, a usual coating method such as a fluidized coating method or a centrifugal fluidized coating method, may be employed. For example, by using a centrifugal fluidized granulation coating apparatus, the granulated core material is supplied together with the first coating agent and water or alcohol in the predetermined proportions for coating treatment, followed by drying.

As described in the foregoing, the present invention provides a feed additive for ruminants wherein the core material composed essentially of an acid salt of a basic amino acid is separated from a polymer substance of the second coating layer sensitive in the acidic region by coating it with a first coating layer of at least one member selected from the group consisting of a neutral or weakly acidic organic substance, a substantially neutral fine powder of inorganic substance, a nonionic hydrophilic polymer substance and an anionic hydrophilic polymer substance, so that the feed additive is excellent in the protection of the core material in the rumen and in the releasability in the abomasum. Among these first coating agents, it is particularly preferred to employ the fine powder of inorganic substance, since it is thereby possible to attain excellent performance for the protection even when the first coating layer is very thin. Further, it is also preferred to employ the neutral or weakly acidic organic substance in that it is thereby possible to provide also a biologically active substance such as an amino acid other than the basic amino acid of the core material.

SECOND COATING LAYER

In the present invention, the surface of the particles treated by the first coating treatment is coated with a second coating layer.

The second coating is intended to protect the particles having the first coating layer in a stable condition during the retention in the rumen for a long period of time and to let the core substance readily elute in the abomasum in a relatively short period of retention time. Accordingly, as the second coating agent, the one which is stable in the weakly acidic to weakly alkaline condition corresponding to the gastric fluid in the rumen of the ruminants and which is capable of being disintegrated, swelled or dissolved in a strongly acidic condition corresponding to the gastric fluid in the abomasum, i.e. a polymer substance soluble or swellable in water in an acidic region of pH 5.5 or lower, is used.

Specific examples of such a second coating agent include, for example, the following:

A cellulose derivative such as benzylaminomethyl cellulose, dimethylaminomethyl cellulose, diethylaminomethyl cellulose, piperidylethylhydroxyethyl cellulose, cellulose acetate diethylamino acetate, cellulose acetate dibutylaminohydroxypropyl ether, ethyl cellulose-N,N-diethylaminohydroxypropyl ether or ethyl cellulose pyridinohydroxypropyl ether; an acetate derivative such as an N,N-diethylvinylamine vinyl acetate copolymer, a vinylpiperidine vinyl acetate copolymer, a vinylbenzylamine vinyl acetate copolymer, a polyvinyldiethylaminoacetoacetal, a polyvinylbenzylaminoacetoacetal, a vinylpiperidylacetoacetal vinyl acetate copolymer, or a polyvinylacetaldiethylamino acetate; polydiethylaminomethylstyrene, or polydiethanolaminomethylstyrene; polydimethylaminoethyl methacrylate, a dimethylaminoethyl acrylate.methyl methacrylate copolymer, a dimethylaminoethyl methacrylate.methyl methacrylate copolymer, or a 2-(4-morpholino)ethyl acrylate.methyl methacrylate copolymer; a polyvinylpyridine such as poly-2-methyl-5-vinylpyridine, poly-2-ethyl-5-vinylpyridine, poly-2-vinylpyridine or poly-4-vinylpyridine; a vinylpyridine styrene copolymer such as a 2-vinylpyridine.styrene copolymer, a 4-vinylpyridine.styrene copolymer, a 2-ethyl-5-vinylpyridine.styrene copolymer, or a 2-methyl-5-vinylpyridine.styrene copolymer; a vinylpyridine.acrylonitrile copolymer such as a 2-vinylpyridine.acrylonitrile copolymer, a 2-ethyl-5-vinylpyridine.acrylonitrile copolymer, or a vinylethylpyridine.acrylonitrile copolymer; a vinylpyridine methyl methacrylate copolymer such as a 2-vinylpyridine.methyl methacrylate copolymer, or a 4-vinylpyridine.methyl methacrylate copolymer; a vinylpyridine.butadiene copolymer such as a 2-vinylpyridine.butadiene copolymer; a copolymer of 2-vinylpyridine with butadiene and styrene, or with styrene and methyl methacrylate, such as a 2-vinylpyridine.butadiene.styrene copolymer, or a 2-vinylpyridine.styrene.methyl methacrylate copolymer; a copolymer of acrylamide or methacrylamide with acrylonitrile or styrene, such as an N,N-dimethylaminopropylacrylamide.acrylonitrile copolymer, an N,N-dimethylaminopropylacrylamide styrene copolymer, an N,N-dimethylaminopropyl methacrylamide.acrylonitrile copolymer, or an N,N-dimethylaminopropyl methacrylamide.styrene copolymer; a reaction condensation product of terephthalic acid or maleic acid with N-n-butyldiethanolamine; and a benzylamine adduct of a propylene glycol.maleic acid polyester.

Among the above-mentioned second coating agents, preferred are a polymer substance containing an amino group and a polymer substance containing a basic nitrogen. Specifically, preferred are a copolymer of dimethylaminoethyl methacrylate with an alkyl (meth)acrylate, and a copolymer of a vinylpyridine selected from the group consisting of 2-methyl-5-vinylpyridine, 2-vinylpyridine, 4-vinylpyridine, 2-vinyl-6-methylpyridine and 2-vinyl-5-methylpyridine, with styrene or an acryl compound selected from the group consisting of an alkyl methacrylate, an alkyl acrylate and acrylonitrile.

The above-mentioned second coating agent may contain a fusion-preventing agent such as talc, aluminum, mica, silica, kaolin, bentonite, diatomaceous earth, stearic acid, aluminum stearate, or magnesium stearate. Further, various supplementary additives may be employed, when the second coating layer is formed.

The second coating agent may be used in an amount sufficient to protect the core material in a stable state during the retention of the coated particles in the rumen of the ruminant and to let the core material readily elute in the abomasum in a relatively short retention time. The amount varies depending upon the size of the particles or the type of the second coating agent, but is usually within a range of from 10 to 200% by weight, preferably from 15 to 80% by weight, based on the particles prior to the coating.

For the second coating, any one of conventional coating methods including a pan coating method, a fluidized coating method and a centrifugal fluidized coating method, may be employed. For the second coating, the coating agent is usually used as dissolved in a suitable solvent such as methylene chloride, chloroform, methanol, ethanol, isopropanol, ethyl acetate, acetone, methyl ethyl ketone or toluene. However, it may be used in the form of an emulsion by means of an emulsifier. Further, the above-mentioned fusion preventing agent may be combined in a suspended state for the coating.

The feed additive for ruminants of the present invention thus obtained is required to have a size suitable for oral administration to the ruminants. It is usually preferred to have a diameter of from 0.4 to 5 mm, particularly from 0.8 to 3.5 mm. Further, the specific gravity of the feed additive is preferably at a level of from 1 to 1.4, so that it is close to the specific gravity of the gastric fluid of ruminants, whereby it can be avoided that the retention time of the feed additive in the stomach is unduly prolonged.

Now, the present invention will be described in further detail with reference to Examples. However, it should be understood that the present invention is by no means restricted to such specific Examples. In the following Examples and Comparative Examples, "%" means "% by weight" unless otherwise specified.

The evaluation of the feed additive to be practically useful for ruminants was conducted by the following standards by the following test methods.

TEST METHODS

Into an Erlenmeyer flask having an internal capacity of 300 ml, 1 g of a sample was introduced, and a McDougall buffer solution* corresponding to the rumen of ruminants or a Clark Lubs buffer solution** corresponding to the abomasum was added in an amount of 200 ml. The flask was shaked in a constant temperature tank of 39±0.5° C. with reciprocation of 91 times/min at an amplitude of 4 cm. The eluted amount of the biologically active substance was measured by a high performance liquid chromatography upon expiration of 24 hours in the case of the McDougall buffer solution and upon expiration of from 2 to 3 hours in the case of the Clark Lubs buffer solution.

EVALUATION STANDARDS

The evaluation was made on such standards that when the sample was shaked for 24 hours in the McDougall buffer solution, at least 65%, preferably at least 75%, of the amino acid salt in the sample was maintained to be stable, and when it was shaked for 3 hours in the Clark Lubs buffer solution, the major portion of the biologically active substance in the sample eluted or was released.

MCDOUGALL BUFFER SOLUTION*

Prepared by dissolving 7.43 g of sodium hydrogencarbonate, 7.0 g of disodium phosphate.$12H_2O$, 0.34 g of sodium chloride, 0.43 g of potassium chloride, 0.10 g of magnesium chloride.$6H_2O$ and 0.05 g of calcium chloride in 1,000 ml of water and saturating carbon dioxide gas (pH 6.8).

CLARK LUBS BUFFER SOLUTION**

Prepared by adding 50 ml of 0.2N potassium chloride and 10.6 ml of 0.2N hydrochloric acid to 139.4 ml of water (pH 2.0).

EXAMPLE 1

(a) Granulation of the core material

Into a centrifugal fluidized granulation coating apparatus (CF-360, Freund Sangyo K.K.), 180 g of crystals of L-lysine hydrochloride having a particle size of from 20 to 24 mesh were charged as seed cores, and granulation was conducted by gradually adding 2,200 g of a 10:1 mixture of L-lysine hydrochloride and fine crystalline cellulose (disintegrator) under rotation while spraying 1,630 g of a 4% aqueous solution of hydroxypropyl cellulose as a binder. The granules thus obtained were dried in a fluidized bed dryer until the water content became less than 1% by weight and classified, by means of a standard sieve to obtain granules of from 10 to 12 mesh containing 89.5% of L-lysine hydrochloride.

The content of the amino acid in the particles was obtained by dissolving 1 g of the sample in 200 ml of the Clark Lubs buffer solution and quantitatively analyzing the content by high performance liquid chromatography. The quantitative analysis was conducted in the same manner also in the subsequent Examples and Comparative Examples.

(b) First coating 2,000 g of the granules of L-lysine hydrochloride obtained in the above step (a) were charged into a centrifugal fluidized granulation coating apparatus, and coating treatment was conducted by supplying 880 g of a fine powder of D,L-methionine as the first coating agent under rotation, while spraying 1,000 g of a 4% aqueous solution of hydroxypropyl cellulose as a binder, followed by drying in a fluidized bed dryer, to obtain a first coating product having a particle size of from 9 to 10 mesh coated with D,L-methionine containing 64.5% of L-lysine hydrochloride, 25.8% of D,L-methionine and 9.7% of cellulose + hydroxypropyl cellulose.

Among the components in the particles, amino acids were quantitatively analyzed by the method as described in the step (a). The amounts of other components were obtained by subtracting the amounts of amino acids from the weight of the particles. In the susequent Examples and Comparative Examples, the amounts of components were determined in the same manner.

(c) Second coating

A mixture comprising a copolymer (reduced viscosity at a concentration of 0.5 g/dl in ethanol: $\eta_{sp/c}=1.30$) of 70% of 4-vinylpyridine with 30% of styrene and stearic acid (fusion-preventing agent) in a 1/6 amount of the copolymer, was dissolved in ethanol to obtain an ethanol solution having a concentration of 4%. This ethanol solution was sprayed from a nozzle, and at the same time, talc was gradually continuously supplied in small portions in the form of a powder. The solution and the talc powder (fusion preventing agent) were supplied in such amounts that the weight ratio of the copolymer:talc powder:stearic acid would be 30:65:5 and used as the second coating agent.

600 g of the first coating product obtained in the above step (b) was supplied to a fluidized coating apparatus and a second coating layer was formed thereon by means of 2,060 g of the ethanol solution of the copolymer and stearic acid and 192 g of talc powder. After coating, the coated product was dried at 70° C. for 5 hours to obtain 833 g of a second coating product. The proportion of the second coating layer in the entire particles, was 28%.

The specific gravity (as measured by an air comparative type specific gravity meter, the same applies in the subsequent Examples) of the particles of the second coating product thus obtained was 1.10.

The coating apparatus is connected with a suction duct for waste gas, whereby the polymer solution sprayed in the coating apparatus and the fine solid particles added during the formation of the first coating layer or the second coating layer, are effectively used, and the proportion of the materials deposited is usually from 70 to 90%, although it varies depending upon the operational conditions. In the following Examples and Comparative Examples, the amount to be coated was predetermined prior to the coating operation. To form a coating layer of a predetermined amount, after the coating, the coated product was dried in a hot air-circulating oven at 70° C. for 5 hours, then the weight was measured at room temperature to obtain the coated amount, and the operational cycle of coating-drying-weight measurement was repeated until the predetermined amount was obtained.

The feed additive thus obtained was subjected to shaking in the McDougall buffer solution at 39° C. for 24 hours, whereupon L-lysine hydrochloride and D,L-methione in the feed additive were found to be maintained in a total amount of 97%. Further, when shaked in the Clark Lubs buffer solution at 39° C. for 2 hours, L-lysine hydrochloride and D,L-methionine eluted in a total amount of 95%, and when shaked for 3 hours, they eluted 100%.

COMPARATIVE EXAMPLE 1

The operation was conducted in the same manner as in Example 1 except that in Example 1, the first coating treatment of the step (b) with D,L-methionine was omitted. After shaking in the McDougall buffer solution at 39° C. for 24 hours, L-lysine hydrochloride in the particles thus obtained was found to be maintained in an amount of only 22.5%. When shaked in the Clark Lubs buffer solution at 39° C. for 3 hours, L-lysine hydrochloride eluted 99.5%.

EXAMPLE 2

(a) Granulation of the core material

Granules of L-lysine hydrochloride were prepared in the same manner as in the step (a) in Example 1.

(b) First coating

The coating treatment was conducted in the same manner as in Example 1 except that 2,000 g of the granules of L-lysine hydrochloride obtained in the above step (a) were used and 900 g of fine powder of L-leucine was used as the coating agent. The coated granules were dried in a fluidized bed type dryer to obtain a first coating product coated with L-leucine and having a particle size of from 9 to 10 mesh, which contained 63.2% of L-lysine hydrochloride, 27.2% of L-leucine and 9.6% of cellulose+hydroxypropyl cellulose.

(c) Second coating

Ethanol was added to a mixture of an N,N-dimethylaminoethyl methacrylate.methyl methacrylate.butyl methacrylate copolymer (Eudragit E100, tradename, Röhm Pharma Co.), aluminum powder and talc powder (weight ratio of 70:15:15) to bring the copolymer concentration to 5%, and the mixture was stirred at room temperature to obtain a slurry solution for coating.

800 g of the first coating product obtained in the above step (b) was supplied to a fluidized coating apparatus, and 5,644 g of the above slurry solution for coating was sprayed to form the second coating layer. The coated product was dried at 70° C. for 5 hours to obtain 1,143 g of a second coating product. The proportion of the second coating layer in the entire particles was 30%.

The particles of the second coating product thus obtained were subjected to shaking in the McDougall buffer solution at 39° C. for 24 hours, whereupon L-lysine hydrochloride and L-leucine in the particles were found to be maintained in a total amount of 92%. Further, when shaked in the Clark Lubs buffer solution at 39° C. for 2 hours, L-lysine hydrochloride and L-leucine eluted in a total amount of 100%.

EXAMPLE 3

(a) Granulation of the core material

Granules of L-lysine hydrochloride were prepared in the same manner as in the step (a) in Example 1.

(b) First coating

The coating treatment was conducted in the same manner as in Example 1 except that 2,000 g of the granules of L-lysine hydrochloride obtained in the above step (a) were used and 900 g of fine powder of L-triptophan was used as the coating agent. The coated granules were dried in a fluidized bed type dryer to obtain a first coating product coated with L-triptophan and having a particle size of from 9 to 10 mesh, which contained 63.0% of L-lysine hydrochloride, 26.7% of L-triptophan and 10.3% of cellulose+hydroxypropyl cellulose.

(c) Second coating

A mixture comprising a 2-vinylpyridine.styrene copolymer (weight ratio:70:30, reduced viscosity as measured at a concentration of 0.5 g/dl in ethanol: $\eta_{sp/c}=1.05$) and stearic acid (fusion preventing agent) in an amount of 1/6 of the copolymer, was dissolved in ethanol to obtain an ethanol solution having a concentration of 4%. While spraying this ethanol solution, talc was supplied in the form of a powder to provide a second coating agent comprising the copolymer:talc powder:stearic acid in a weight ratio of 30:65:5.

The first coating product obtained in the above step (b) was supplied to a fluidized coating apparatus, and the above second coating agent was sprayed for coating treatment until the proportion of the coating layer became 30% of the total weight of the particles after coating.

The particles of the second coating product thus obtained were subjected to shaking in the McDougall buffer solution at 39° C. for 24 hours, whereupon L-lysine hydrochloride and L-tryptophan in the particles were found to be maintained in a total amount of 99%. Further, when shaked in the Clark Lubs buffer solution at 39° C. for 2 hours, L-lysine hydrochloride and L-tryptophan eluted in a total amount of 88%, and when shaked for 3 hours, they eluted 100%.

EXAMPLE 4

(a) Granulation of the core material

Into a centrifugal fluidized granulation coating apparatus, 360 g of sucrose having a particle size of from 20 to 24 mesh were charged as seed cores, and granulation was conducted under such condition that 2,100 g of a mixture of L-histidine hydrochloride and talc (filler) (20:1) was gradually added under rotation, and 1,650 g of a 4% water-ethanol solution (water:ethanol= 40:60) of hydroxypropyl cellulose was sprayed. The granules thus obtained were dried in a fluidized bed type dryer and classified to obtain granules of from 9 to 10 mesh containing 79.5% of L-histidine hydrochloride.

(b) First coating 2,000 g of the granules of L-histidine hydrochloride obtained in the above step (a) were subjected to the same coating treatment as in Example 1 and dried in a fluidized bed type dryer to obtain a first coating product having a particle size of from 8 to 10 mesh coated with D,L-methionine, which contained 54.9% of L-histidine hydrochloride, 30.0% of D,L-methionine, 9.9% of sucrose and 5.2% of talc+hydroxypropyl cellulose.

(c) Second coating

A slurry solution for second coating was prepared in the same manner as in Example 2.

The first coating product obtained in the above step (b) was supplied to a fluidized coating apparatus, and the above-mentioned slurry solution for second coating was sprayed for second coating treatment until the proportion of the coating layer became 30% of the total weight of the particles after coating. The particles of the second coating product thus obtained were subjected to shaking in the McDougall buffer solution at 39° C. for 24 hours, whereupon L-histidine hydrochloride and D,L-methionine in the particles were found to be maintained in a total amount of 95%. Further, when shaked in the Clark Lubs buffer solution at 39° C. for 2 hours, L-histidine hydrochloride and D,L-methionine eluted in a total amount of 92%, and when shaked for 3 hours, they eluted 98%.

COMPARATIVE EXAMPLE 2

The operation was conducted in the same manner as in Example 4 except that in Example 4, the first coating treatment of the step (b) with D,L-methionine was omitted. The particles thus obtained were subjected to shaking in the McDougall buffer solution at 39° C. for 24 hours, whereupon L-histidine hydrochloride in the particles was found to be maintained in an amount of only 18.5%. Further, when shaked in the Clark Lubs buffer solution at 39° C. for 3 hours, L-histidine hydrochloride eluted 100%.

EXAMPLE 5

(a) Granulation of the core material

Into a centrifugal fluidized granulation coating apparatus, 350 g of sucrose having a particle size of from 20 to 24 mesh was charged as seed cores, and granulation was conducted by adding a mixture comprising 1,500 g of L-lysine hydrochloride, 500 g of glucose and 300 g of kaolin (filler) while spraying 650 g of a water methanol solution (water:methanol=70:30) containing 2% of hydroxypropyl cellulose. The granules thus obtained were dried in a fluidized bed type dryer and classifed to obtain granules of from 10 to 12 mesh.

(b) First coating 800 g of the granules containing L-lysine hydrochloride obtained in the above step (a) were charged into a centrifugal fluidized granulation coating apparatus and subjected to coating treatment by supplying 230 g of starch (first coating agent) while spraying 940 g of a water-methanol (40:60) solution containing 4% of hydroxypropyl cellulose. The coated granules were dried in a fluidized bed type dryer and further classified to obtain particles of the first coating product having a particle size of from 9 to 10 mesh.

(c) Second coating

The particles of the first coating product obtained in the above step (b) were charged into a fluidized coating apparatus, and coating treatment was conducted by spraying as the second coating agent talc powder and the ethanol solution of a mixture comprising a 4-vinylpyridine.styrene copolymer and stearic acid in a 1/6 amount thereof as used in the step (c) in Example 4 until the proportion of the coating layer became 29.5% of the total weight of the particles after coating. The particles of the second coating product thus obtained had a specific gravity of 1.18.

The particles of the second coating product thus obtained were subjected to shaking in the McDougall buffer solution at 39° C. for 24 hours, whereupon L-lysine hydrochloride and glucose in the particles were found to be maintained in a total amount of 92%. Further, when shaked in the Clark Lubs buffer solution at 39° C. for 2 hours, L-lysine hydrochloride and glucose eluted in a total amount of 99%.

EXAMPLE 6

(a) Granulation of the core material

Into a centrifugal fluidized granulation coating apparatus, 350 g of granular sucrose having a particle size of from 20 to 24 mesh was charged as seed cores, and granulation was conducted by adding a mixture comprising 2,000 g of L-arginine hydrochloride and 250 g of kaolin while spraying 640 g of a water-methanol (water:methanol =70:30) solution containing 2% of hydroxypropyl cellulose. The granules thus obtained were dried in a fluidized bed type dryer and classified to obtain granules having a particle size of from 10 to 12 mesh.

(b) First coating 700 g of the granules containing L-arginine hydrochloride obtained in the above step (a) were charged into a centrifugal fluidized granulation coating apparatus, and coating treatment was conducted by supplying 250 g of L-threonine (first coating agent) while spraying 820 g of a water-methanol (40:60) solution containing 4% of hydroxypropyl cellulose. Then, the coated granules were dried in a fluidized bed type dryer and classified to obtain particles of the first coating product having a particle size of from 9 to 10 mesh.

(c) Second coating

The particles of the first coating product obtained in the above step (b) was subjected to coating treatment by spraying the same second coating agent as used in the step (c) of Example 1 until the proportion of the coating layer became 25.5% of the total weight of the particles after coating. The particles of the second coating product thus obtained had a specific gravity of 1.14.

The particles of the second coating product thus obtained were subjected to shaking in the McDougall buffer solution at 39° C. for 24 hours, whereupon L-arginine hydrochloride and L-threonine in the particles were found to be maintained in a total amount of 90%. Further, when shaked in the Clark Lubs buffer solution at 39° C. for 2 hours, L-arginine hydrochloride and L-threonine eluted in a total amount of 100%.

EXAMPLE 7

(a) Granulation of the core material

Into a centrifugal fluidized granulation coating apparatus, 350 g of granular sucrose having a particle size of from 20 to 24 mesh was charged as seed cores, and granulation was conducted by adding a mixture comprising 1,000 g of L-lysine hydrochloride, 1,000 g of D,L-methionine and 200 g of Microcel M-35 (fine hollow sodium borosilicate, filler, manufactured by Asahi Glass Co., Ltd.) while spraying 640 g of a water-methanol (water:methanol=40:60) solution containing 4% of hydroxypropyl cellulose. The granules thus obtained were dried in a fluidized bed type dryer and classified to obtain granules having a particle size of from 10 to 12 mesh.

(b) First coating 1,000 g of the granules obtained in the above step (a) were charged into a centrifugal fluidized granulation coating apparatus, and coating treatment was conducted by supplying 400 g of casein (first coating agent) while spraying 400 g of a water-methanol (40:60) solution containing 4% of hydroxypropyl cellulose. The coated granules thus obtained were dried by a fluidized bed type dryer and classified to obtain particles of the first coating product having a particle size of from 9 to 10 mesh.

(c) Second coating

The particles of the first coating product obtained in the above step (b) were subjected to coating treatment by spraying the same second coating agent as used in the step (c) of Example 3 until the proportion of the coating layer became 24.0% of the total weight of the particles after coating.

The particles of the second coating product thus obtained had a specific gravity of 1.11.

The particles of the second coating product thus obtained were subjected to shaking in the McDougall buffer solution at 39° C. for 24 hours, whereupon L-lysine hydrochloride and D,L-methionine were found to be maintained in a total amount of 98%. Further, when shaked in the Clark Lubs buffer solution at 39° C. for 3 hours, L-lysine hydrochloride and D,L-methionine eluted in a total amount of 96.5%.

EXAMPLE 8

(a) Granulation of the core material

Into the same centrifugal fluidized granulation coating apparatus (CF-360) as used in Example 1, spherical sucrose (Nonpareil 103, tradenamde, particle size: 20–24 mesh, manufactured by Freund Sangyo K. K.) was charged as seed cores, and granulation was conducted by gradually adding a uniformly mixed powder comprising 2,000 g of L-lysine hydrochloride and 400 g of talc while spraying under rotation 1,600 g of a 4% aqueous solution of hydroxypropyl cellulose as the binder. The granules thus obtained were dried in a fluidized bed type dryer at 70° C. for 5 hours to obtain milky white particles. The particles were classified by means of a JIS standard sieves to obtain granules of from 9 to 10 mesh. The particles thus obtained had a specific gravity of 1.47, a bulk density of 0.49 and a lysine hydrochloride content of 0.71 g/g.

(b) First coating 700 g of the granules of lysine hydrochloride obtained in the above step (a) were charged into the same apparatus (CF-360) as used above, and coating treatment was conducted by supplying fine powder of D,L-methionine as the first coating agent in an amount as identified in the following Table 1 while spraying under rotation a 4% aqueous solution of hydroxypropyl cellulose as the binder. Then, the coated granules were dried in a fluidized bed type dryer. The particles thus obtained were classified by means of a JIS standard sieve to obtain particles having the surface coated with methionine having a particle size of from 9 to 10 mesh. The weight ratio of the methionine layer in the total amount of the particles obtained from the amount of the methionine used and the coated amount, is shown in Table 1.

(c) Second coating

A copolymer (reduced viscosity at a concentration of 0.5 g/dl in ethanol: $\eta_{sp/c}=1.30$) of 70% of 4-vinylpyridine with 30% of styrene was dissolved in ethanol to obtain a 3 wt% solution. This solution and talc powder were used as the second coating agent in such proportions that the weight ratio of the copolymer:the talc powder became 30:70. The second coating agent was coated until the proportion of the coating layer became from 20 to 30%, as shown in Table 1.

The particles thus obtained were evaluated by shaking tests in buffer solutions. In the neutral environment, they exhibited excellent protection, and in the acidic environment, the content was readily released in about one hour and a half.

TABLE 1

Preparation of particles having D,L-methionine as the first coating layer and their properties

| | | Example No. | | | |
|---|---|---|---|---|---|
| | | 8-1 | 8-2 | 8-3 | 8-4 |
| | Granules charged (g) | 700 | 700 | 700 | 700 |
| | D,L-methionine charged (g) | 48 | 120 | 50 | 150 |
| First coating layer | Methionine content in the particles having a methionine coating layer (wt %) | 5.0 | 10.0 | 4.8 | 14.8 |
| Second coating layer | Weight ratio of the coating layer in the entire particles (wt %) | 20 | 30 | 20 | 30 |
| Shaking test | Remaining rate of L-lysine hydrochloride and methionine in the McDougall buffer solution (%); pH 6.8/24 hr. | 85 | 99 | 90 | 100 |
| | Eluted rate of L-lysine hydrochloride and methionine in the Clark Lubs buffer solution (%); pH 2/1.5 hr. | 100 | 100 | 100 | 100 |

COMPARATIVE EXAMPLE 3

Granulation of the core material

Into the same centrifugal granulation coating apparatus as used in Example 1, 360 g of spherical sucrose (Nonpareil 103, tradename, particle size: 20–24 mesh, manufactured by Freund Sangyo K. K.) was added, and granulation was conducted by gradually adding a uniform mixture comprising 1,600 g of L-lysine hydrochloride and 400 g of basic magnesium carbonate and spraying a 4% aqueous solution of hydroxypropyl cellulose as the binder, under rotation.

The granules thus obtained were dried by a fluidized bed type dryer at 70° C. for 5 hours. The granules were classified by means of a JIS standard sieve to obtain granules of from 9 to 10 mesh. The lysine hydrochloride content of the particles thus obtained was 0.66 g/g, and the particles were colored slightly yellow.

Coating

Without conducting the first coating treatment, the second coating agent as used in Example 8 was coated until the proportion of the coating layer became 20 wt%.

The feed additive thus obtained was subjected to shaking in the McDougall buffer solution at 39° C. for 24 hours, whereupon L-lysine hydrochloride was found to be maintained in an amount of only 55%. When shaken in the Clark Lubs buffer solution at 39° C. for 1.5 hours, it was released 100%.

EXAMPLE 9

(a) Granulation of the core material

Into a centrifugal fluidized granulation coating apparatus (CF-360, Freund Sangyo K. K.), 200 g of crystals of L-lysine hydrochloride having a particle size of from 20 to 24 mesh were charged as seed cores, and granulation was conducted by gradually adding 2,500 g of a 10:1 mixture of L-lysine hydrochloride and fine crystalline cellulose (disintegrator) under rotation while spraying 1,800 g of a 4% aqueous solution of hydroxypropyl cellulose as a binder. The granules thus obtained were dried in a fluidized bed dryer and classified by means of a standard sieve to obtain granules of from 9 to 10 mesh containing 89.5% of L-lysine hydrochloride.

(b) First coating 1,000 g of the granules of L-lysine hydrochloride obtained in the above step (a) were charged into a centrifugal fluidized granulation coating apparatus, and coating treatment was conducted by gradually supplying 700 g of a fine powder of talc passing through a 200 mesh sieve as the first coating agent, under rotation while spraying 800 g of a 4% aqueous solution of hydroxypropyl cellulose as a binder, followed by drying in a fluidized bed dryer, to obtain 1,560 g of particles of the first coating product. The proportion of the first coating layer as calculated from the increase in the weight was 35.9%.

(c) Second coating

Ethanol was added to a mixture of an N,N-dimethylaminoethyl methacrylate.methyl methacrylate.butyl methacrylate copolymer (Eudragit E100, tradename, Röhm Pharma Co.), aluminum powder and talc powder (weight ratio of 70:15:15) to bring the copolymer concentration to 5%, and the mixture was stirred at room temperature to obtain a slurry solution for coating.

800 g of the first coating product obtained in the above step (b) was supplied to a fluidized coating apparatus (CF-360), and 4,560 g of the above slurry solution for coating was sprayed under rotation to form a coating layer. After coating, the coated product was left to stand at 70° C. for 5 hours for drying to obtain 994 g of particles of the second coating product. The proportion of the second coating layer in the entire particles was 19.5%.

The L-lysine hydrochloride content in 1 g of the particles of the second coating product thus obtained was 0.48 g. After shaking in the McDougall buffer solution at 39° C. for 24 hours, L-lysine hydrochloride was found to be maintained 98.1%. Further, when shaked in the Clark Lubs buffer solution at 39° C. for 2 hours, L-lysine hydrochloride eluted 95%, and when shaked for 3 hours, L-lysine hydrochloride eluted 100%.

COMPARATIVE EXAMPLE 4

800 g of the granules of from 9 to 10 mesh containing 89.5% of L-lysine hydrochloride obtained in the step (a) in Example 9 were charged into a granulation coating apparatus (CF-360), and second coating treatment was conducted with 4,850 g of the slurry solution comprising Eudragit E100, aluminum powder and talc powder as used in the step (c) in Example 9, directly without conducting first coating treatment with fine powder of talc as in the step (b) in Example 9. The proportion of the second coating layer was 20.5% of the total weight of the particles after coating.

The L-lysine hydrochloride content in 1 g of the particles thus obtained was 0.72 g. After shaking in the McDougall buffer solution at 39° C. for 24 hours, L-lysine hydrochloride was found to be maintained only 22.5%. When shaked in the Clark Lubs buffer solution at 39° C. for 3 hours, L-lysine hydrochloride eluted 99.5%.

EXAMPLE 10

(a) Granulation of the core material

Granules of L-lysine hydrochloride were prepared in the same manner as in the step (a) in Example 9.

(b) First coating 600 g of the granules of L-lysine hydrochloride obtained in the above step (a) were charged into a centrifugal granulation coating apparatus (CF-360), and the first coating was conducted in the same manner as in Example 9 except that the 4% aqueous solution of hydroxypropyl cellulose was used in an amount of 440 g, and talc was used in the amount of 370 g, to obtain 994 g of the first coating product. The proportion of the first coating layer as calculated from the increase in the weight was 33.3%.

(c) Second coating 400 g of the first coating product obtained in the above step (b) was supplied to a fluidized coating apparatus, and second coating treatment was conducted with 3,160 g of the ethanol slurry solution containing a mixture of Eudragit E100, aluminum powder and talc powder as used in the step (c) in Example 9. The proportion of the second coating layer was 26.7% of the total weight of the particles after coating.

The L-lysine hydrochloride content in 1 g of the particles of the second coating product thus obtained was 0.44 g. After shaking in the McDougall buffer solution at 39° C. for 24 hours, L-lysine hydrochloride was found to be maintained 100%. Further, when shaked in the Clark Lubs buffer solution at 39° C. for 3 hours, L-lysine hydrochloride eluted in 100%.

EXAMPLE 11

(a) Granulation of the core material

Granules of L-lysine hydrochloride were prepared in the same manner as in the step (a) in Example 9.

(b) First coating 600 g of the granules of L-lysine hydrochloride obtained in the above step (a) were charged into a centrifugal fluidized granulation coating apparatus, and coating was conducted by supplying 400 g of fine powder of silica passing through a 200 mesh sieve as the first coating agent while spraying 470 g of a 4% aqueous solution of hydroxypropyl cellulose as a binder, followed by drying in a fluidized bed type dryer to obtain 942 g of particles of the first coating product. The proportion of the first coating layer as calculated from the increase in the weight was 36.3%.

(c) Second coating 400 g of the first coating product obtained in the above step (b) was supplied to a fluidized coating apparatus, and second coating treatment was conducted with 2,430 g of the ethanol slurry solution containing a mixture of Eudragit E100, aluminum powder and talc powder as used in the step (c) in Example 9. The proportion of the second coating layer was 20.5% of the total weight of the particles after coating.

The L-lysine hydrochloride content in 1 g of the particles of the second coating product thus obtained was 0.47 g. After shaking in the McDougall buffer solution at 39° C. for 24 hours, L-lysine hydrochloride was found to be maintained 97.1%. Further, when shaked in the Clark Lubs buffer solution at 39° C. for 2 hours, L-lysine hydrochloride eluted 98%.

EXAMPLE 12

(a) Granulation of the core material

Granules of L-lysine hydrochloride were prepared in the same manner as in the step (a) in Example 9.

(b) First coating

Coating treatment was conducted in the same manner as in the step (b) in Example 9 except that instead of the talc powder, fine powder of aluminum passing through a 200 mesh sieve was employed, to obtain a first coating product, whereby the proportion of the aluminum coating layer was 33.9% of the total weight of the particles after coating.

(c) Second coating 600 g of the first coating product obtained in the above step (b) was supplied to a fluidized coating apparatus, and a second coating layer was formed by adding 160 g of talc powder while spraying 1,730 g of the coating solution as described in the step (c) in Example 1. The coated product was left to stand at 70° C. for 5 hours for drying, whereupon the yield was 796 g. The proportion of the second coating layer was 24.6% of the total weight of the particles after coating.

The L-lysine hydrochloride content in 1 g of the particles of the second coating product thus obtained was 0.45 g. After shaking in the McDougall buffer solution at 39° C. for 24 hours, L-lysine hydrochloride was found to be maintained 100%. Further, when shaked in the Clark Lubs buffer solution at 39° C. for 3 hours, L-lysine hydrochloride eluted 100%.

EXAMPLE 13

(a) Granulation of the core material

Granules of L-histidine hydrochloride were prepared in the same manner as in the step (a) in Example 4.

(b) First coating 400 g of the granules of L-histidine hydrochloride obtained in the above step (a) were charged into a centrifugal fluidized granulation coating apparatus, and coating was conducted by supplying 270 g of fine powder of aluminum passing through a 200 mesh sieve as the first coating agent while spraying 320 g of a 4% aqueous solution of hydroxypropyl cellulose as a binder under rotation, followed by drying in a fluidized bed type dryer to obtain 617 g of particles of the first coating product. The proportion of the first coating layer as calculated from the increase in the weight was 35.2%.

(c) Second coating 400 g of the first coating product obtained in the above step (b) was supplied to a fluidized coating apparatus, and coating was conducted by adding 110 g of talc powder while spraying 1,150 g of the same coating solution as used in the step (c) in Example 3, followed by drying in a fluidized bed dryer to obtain 523 g of particles of the second coating product. The proportion of the second coating layer as calculated from the increase in the weight was 23.5%. The particles of the second coating product thus obtained were subjected to shaking in the McDougall buffer solution at 39° C. for 24 hours, whereupon L-histidine hydrochloride was found to be maintained 95.8%. Further, when shaked in the Clark Lubs buffer solution at 39° C. for 2 hours, L-histidine hydrochloride eluted 100%.

EXAMPLE 14

(a) Granulation of the core material

Into a centrifugal fluidized granulation coating apparatus (CF-360), 350 g of L-lysine hydrochloride having a particle size of from 20 to 24 mesh was charged as seed cores, and granulation was conducted by adding a mixture comprising 650 g of L-lysine hydrochloride, 1,000 g of D,L-methionine, 200 g of Microcel M-35 (fine hollow sodium borosilicate, specific gravity controlling agent, manufactured by Asahi Glass Co., Ltd.) and 150 g of bentonite (filler), while spraying a water-ethanol (water:ethanol=40:60) solution containing 4% of hydroxypropyl cellulose. The granules thus obtained were dried in a fluidized bed type dryer and further classified to obtain granules having a particle size of from 10 to 12 mesh and a specific gravity of 1.20.

(b) First coating 1,000 g of the granules containing L-lysine hydrochloride obtained in the above step (a) were charged into a centrifugal fluidized granulation coating apparatus, and coating treatment was conducted by supplying 400 g of fine powder of talc passing through a 200 mesh sieve as the first coating agent while spraying a water-ethanol (40:60) solution containing 4% of a hydroxypropyl cellulose as a binder, under rotation. Then, the coated granules were dried in a fluidized bed type dryer and further classified to obtain a first coating product having a particle size of from 9 to 10 mesh and a specific gravity of 1.25.

(c) Second coating

By using the same second coating agent as used in the step (c) in Example 13, the first coating product obtained in the above step (b) was subjected to coating treatment until the proportion of the second coating layer became 25.0% of the total weight of the particles after coating, in the same manner as in the step (c) in Example 13. The particle size of the particles of the second coating product thus obtained was from 1.68 to 2.38 mm, and the specific gravity was 1.08.

Further, L-lysine hydrochloride and D,L-methionine in the particles of the second coating product were found to be maintained 99.2% in total after shaking in the McDougall buffer solution at 39° C. for 24 hours. Further, when shaked in the Clark Lubs buffer solution at 39° C. for 3 hours, L-lysine hydrochloride and D,L-methionine eluted 98.5% in total.

EXAMPLE 15

(a) Granulation of the core material

Into a centrifugal fluidized coating apparatus (CF-360), 360 g of spherical sucrose (Nonpareil 103, tradename, particle size: 20–24 mesh, manufactured by Freund Sangyo K. K.) was added as seed cores, and granulation was conducted by gradually adding a uniformly mixed powder comprising 2,000 g of L-lysine hydrochloride and 400 g of talc under rotation, while spraying a 3% aqueous solution of poly N-vinylpyrrolidone (K-90) as a binder.

The granules thus obtained were dried in a fluidized bed type dryer at 70° C. for 5 hours to obtain milky white particles. The particles were classified by means of a JIS standard sieve to obtain granules of from 9 to 10 mesh.

The particles thus obtained had a specific gravity of 1.50, a bulk density of 0.50 and a L-lysine hydrochloride content of 0.71 g/g.

(b) First coating 700 g of the granules of L-lysine hydrochloride obtained in the above step (a) were charged into a centrifugal fluidized coating apparatus, and coating treatment was conducted by supplying fine powder of talc as the frist coating agent in the amount as identified in Table 2, while spraying a 4% aqueous solution of hydroxypropyl cellulose as a binder, followed by drying in a fluidized bed dryer. The dried particles were classified by means of a JIS standard sieve, to obtain particles having the surface coated with talc having a particle size of from 9 to 10 mesh. The amount of talc used and the weight ratio of the talc layer in the total particles obtained from the coated amount are shown in Table 2.

(c) Second coating

A copolymer of 70% of 4-vinylpyridine with 30% of styrene (reduced viscosity at a concentration of 0.5 g/dl in ethanol: $\eta_{sp/c} = 1.30$) was dissolved in ethanol to obtain a 3 wt% ethanol solution. This solution and talc powder were used as the second coating agent in such proportions that the weight ratio of the copolymer:talc powder became 30:70, and coating was conducted until the proportion of the coating layer became from 20 to 26% as identified in Table 2.

The particles thus obtained were evaluated by shaking tests in buffer solutions. In the neutral environment, they exhibited excellent protection, and in the acidic environment, the content was readily released in about 2 hours.

TABLE 2

Preparation of particles having talc as the first coating layer and their properties

|  |  | Example No. | | | |
| --- | --- | --- | --- | --- | --- |
|  |  | 15-1 | 15-2 | 15-3 | 15-4 |
| First coating layer | Granules charged (g) | 700 | 700 | 700 | 700 |
|  | Talc charged (g) | 30 | 90 | 50 | 140 |
|  | Talc content in the particles having a talc coating layer (wt %) | 3.3 | 10.0 | 5.5 | 14.5 |
| Second coating layer | Weight ratio of the coating layer in the entire particles (wt %) | 20 | 26 | 20 | 26 |
| Shaking test | Remaining rate of L-lysine hydrochloride in the McDougall buffer solution (%); pH 6.8/24 hr. | 85 | 97 | 93 | 99 |
|  | Eluted rate of L-lysine hydrochloride in the Clark Lubs buffer soltuion (%); pH 2/2 hr. | 100 | 100 | 100 | 100 |

EXAMPLES 16 to 18

By using the particles composed essentially of L-lysine hydrochloride as prepared in the step (a) in Example 15, a first coating layer was formed in the same manner as in the step (b) in Example 15 except that the type of the inorganic material used for the first coating layer was changed from fine powder of talk to fine powder of aluminum silicate, kaolin or magnesium silicate. The second coating was conducted in the same manner as in the step (c) in Example 15. The results thereby obtained are shown in Table 3.

TABLE 3

Preparation of particles having inorganic material as the coating layer and their properties

|  | Example No. | | |
| --- | --- | --- | --- |
|  | 16 | 17 | 18 |
| Granules charged (g) | 700 | 700 | 700 |
| Type of inorganic material | Aluminum | Kaolin | Magnesium |

TABLE 3-continued

Preparation of particles having inorganic material as the coating layer and their properties

| | | Example No. | | |
|---|---|---|---|---|
| | | 16 | 17 | 18 |
| First coating layer | Amount of inorganic material (g) | silicate 100 | 110 | silicate 100 |
| | Content of inorganic material in the coating layer of particles coated with the inorganic material (wt %) | 10.5 | 11.0 | 10.8 |
| Second coating layer | Weight ratio of the coating layer in the entire particles (wt %) | 20.3 | 21.0 | 20.5 |
| Shaking test | Remaining rate of L-lysine hydrochloride in the McDougall buffer solution (%); pH 6.8/24 hr. | 97.0 | 96.5 | 98.2 |
| | Eluted rate of L-lysine hydrochloride in the Clark Lubs buffer solution (%); pH 2/2 hr. | 100 | 100 | 100 |

EXAMPLE 19

Granulation of the core material

Into a centrifugal fluidized granulation coating apparatus (CF-360, Freund Sangyo K.K.), 320 g of crystals of sucrose having a particle size of from 20 to 24 mesh as seed cores, and granulation was conducted by gradually adding 2,400 g of a 10:2 mixture of L-lysine hydrochloride and talc under rotation while spraying 1,625 g of a 4% aqueous solution of hydroxypropyl cellulose as a binder. The granules thus obtained were dried in a fluidized bed dryer and then classified by means of a standard sieve to obtain granules of from 9 to 10 mesh containing 71.8% of L-lysine hydrochloride.

(b) First coating 2,000 g of the granules of L-lysine hydrochloride obtained in the above step (a) were charged into a centrifugal fluidized granulation coating apparatus, and coating treatment was conducted by spraying 8,538.5 g of a suspension prepared by adding talc to a 5% methanol solution of polyvinylpyrrolidone K-30 (polyvinylpyrrolidone:talc = 10:3), followed by drying in a fluidized bed type dryer to obtain a first coating product.

(c) Second coating 800 g of the first coating product obtained in the above step (b) was supplied to a fluidized coating apparatus, and coating was conducted by adding 292 g of talc powder while spraying 3,120 g of the same coating solution as used in the step (c) in Example 1, followed by drying to obtain 1,133 g of particles of the second coating product. The proportion of the second coating layer as obtained from the increase in the weight was 29.4%.

The particles of the second coating product thus obtained had a L-lysine hydrochloride content of 39.8% and a specific gravity of 1.20.

The coated particles were shaken in the McDougall buffer solution at 39° C. for 24 hours, whereupon L-lysine hydrochloride was found to be maintained 95%. Further, when shaked in the Clark Lubs buffer solution at 39° C. for 3 hours, L-lysine hydrochloride eluted 100%.

COMPARATIVE EXAMPLE 5

Without conducting the first coating treatment with polyvinylpyrrolidone as in the step (b) in Example 19, the second coating treatment with the 4-vinylpyridine.styrene copolymer in the step (c) in Example 19 was applied directly to the granules of from 9 to 10 mesh containing 71.8% of L-lysine hydrochloride obtained by granulating L-lysine hydrochloride in the step (a) in Example 19, until the proportion of the coating layer became 31.0% of the total weight of the particles after coating.

The particles thus obtained were subjected to shaking in the McDougall buffer solution at 39° C. for 24 hours, whereupon L-lysine hydrochloride in the particles was found to be maintained only 24.3%. Further, when shaked in the Clark Lubs buffer solution at 39° C. for 3 hours, L-lysine hydrochloride eluted 99.5%.

EXAMPLE 20

(a) Granulation of the core material

Granules of L-lysine hydrochloride were prepared in the same manner as in the step (a) in Example 19.

(b) First coating 2,000 g of the granules of L-lysine hydrochloride obtained in the above step (a) were charged into a centrifugal fluidized granulation coating apparatus, and coating treatment was conducted by spraying 6,158.7 g of a suspension prepared by adding talc to a 5% methanol solution of hydroxypropyl cellulose (hydroxypropyl cellulose:talc = 10:3), under rotation, followed by drying in a fluidized bed type dryer to obtain a first coating product.

(c) Second coating 800 g of the first coating product obtained in the above step (b) was supplied to a centrifugal fluidized coating apparatus, and coating was conducted by adding 175 g of talc powder while spraying 1,865 g of the coating solution containing the 4-vinylpyridine.styrene copolymer and stearic acid as used in the step (c) in Example 1, under rotation, followed by drying to obtain 1,009 g of particles of the second coating product. The proportion of the second coating layer as obtained from the increase in the weight was 20.7%. The particles of the second coating product thus obtained had a L-lysine hydrochloride content of 46.1% and a specific gravity of 1.11.

The coated particles were shaken in the McDougall buffer solution at 39° C. for 24 hours, whereupon L-lysine hydrochloride was found to be maintained 99%.

Further, when shaked in the Clark Lubs buffer solution at 39° C. for 3 hours, L-lysine hydrochloride eluted 100%.

EXAMPLE 21

(a) Granulation of the core material

Granules of L-lysine hydrochloride were prepared in the same manner as in the step (a) in Example 19.

(b) First coating

In the same manner as in the step (b) in Example 20, a first coating product coated with hydroxypropyl cellulose was prepared.

(c) Second coating 800 g of the first coating product obtained in the above step (b) was charged to a centrifugal fluidized coating apparatus, and coating was conducted by adding 313 g of talc powder while spraying 3,350 g of the coating solution containing the 4-vinylpyridine.styrene copolymer and stearic acid as used in the step (c) in Example 1. The coated product was dried to obtain 1,180 g of particles of the second coating product. The proportion of the second coating layer as obtained from the increase in the weight was 32.2%.

The coated particles were shaked in the McDougall buffer solution at 39° C. for 24 hours, whereupon L-lysine hydrochloride was found to be maintained 100%. Further, when shaked in the Clark Lubs buffer solution at 39° C. for 3 hours, L-lysine hydrochloride eluted 97%.

EXAMPLE 22

(a) Granulation of the core material

Into a centrifugal fluidized granulation coating apparatus, 300 g of crystals of sucrose having a particle size of from 20 to 24 mesh as seed cores, and granulation was conducted by gradually adding 2,100 g of a 20:1 mixture of L-histidine hydrochloride and talc, under rotaion, while spraying 1,125 g of a water-ethanol (water:ethanol=40:60) solution containing 4% of hydroxypropyl cellulose as a binder. The granules thus obtained were dried in a fluidized bed type dryer and then classified to obtain granules of from 9 to 10 mesh containing 81.8% of L-histidine hydrochloride.

(b) First coating 2,000 g of the granules of L-histidine hydrochloride obtained in the above step (a), were charged into a centrifugal fluidized granulation coating apparatus, and coating treatment was conducted by spraying 6,722.4 g of a suspension prepared by adding talc to a 5% methanol solution of hydroxypropyl cellulose (hydroxypropyl cellulose:talc=10:3) under rotation, followed by drying in a fluidized bed type dryer to obtain a first coating product.

(c) Second coating 800 g of the first coating product obtained in the above step (b) was supplied to a centrifugal fluidized coating apparatus, and coating was conducted by adding 208 g of talc powder while spraying 2,025 g of the coating solution containing the 4-vinylpyridine.styrene copolymer and stearic acid as used in the step (c) in Example 1, under rotation. The coated product was dried to obtain 1,030 g of particles of the second coating product. The proportion of the second coating layer as obtained from the increase in the weight was 22.3%.

The particles of the second coating product thus obtained had a L-histidine hydrochloride content of 52.3% and a specific gravity of 1.13.

The coated particles were shaked in the McDougall buffer solution at 39° C. for 24 hours, whereupon L-histidine hydrochloride was found to be maintained 94%. Further, when shaked in the Clark Lubs buffer solution at 39° C. for 3 hours, L-histidine hydrochloride eluted 91%.

EXAMPLE 23

(a) Granulation of the core material

Granules of L-lysine hydrochloride were prepared in the same manner as in the step (a) in Example 19.

(b) First coating 2,000 g of the granules of L-lysine hydrochloride obtained in the above step (a) were charged into a centrifugal fluidized granulation coating apparatus, and coating treatment was conducted by spraying 6,158.7 g of a suspension prepared by adding talc to a 5% methanol solution of hydroxypropyl cellulose (hydroxypropyl cellulose:talc=10:3) under rotation, followed by drying in a fluidized bed type dryer to obtain a first coating product.

(c) Second coating 800 g of the first coating product obtained in the above step (b) was supplied to a centrifugal fluidized coating apparatus, and a second coating layer was formed by spraying 3,360 g of the slurry solution for the second coating as used in the step (c) in Example 2, under rotation. The coated product was dried at 70° C. for 5 hours to obtain 1,004 g of the second coating product. The proportion of the second coating layer was 20.3% of the total amount of the particles after coating.

The particles of the second coating product thus obtained had a L-lysine hydrochloride content of 46.3% and a specific gravity of 1.13.

The coated particles were shaked in the McDougall buffer solution at 39° C. for 24 hours, whereupon L-lysine hydrochloride was found to be maintained 90%. Further, when shaked in the Clark Lubs buffer solution at 39° C. for 3 hours, L-lysine hydrochloride eluted 100%.

EXAMPLE 24

(a) Granulation of the core material

Granules of L-lysine hydrochloride were prepared in the same manner as in the step (a) in Example 19.

(b) First coating 3,000 g of the granules of L-lysine hydrochloride obtained in the above step (a) were charged into a centrifugal fluidized granulation coating apparatus, and coating treatment was conducted by spraying 16,100 g of a suspension prepared by adding talc to a 3% aqueous solution of sodium polyacrylate (sodium polyacrylate:talc =10:3) under rotation, followed by drying in a fluidized bed type dryer to obtain a first coating product.

(c) Second coating 1,000 g of the first coating product obtained in the above step (b) was supplied to a centrifugal fluidized coating apparatus, and coating was conducted by adding 239 g of talc powder while spraying 3,220 g of the coating solution containing the 4-vinylpyridine.styrene copolymer and stearic acid as used in the step (c) in Example 1, under rotation. The coated product was dried to obtain 1,044 g of particles of the second coating product. The proportion of the second coating layer as obtained from the increase in the weight was 23.4%.

The particles of the second coating product thus obtained had a L-lysine hydrochloride content of 46.2% and a specific gravity of 1.18.

The coated particles were shaked in the McDougall buffer solution at 39° C. for 24 hours, whereupon L-lysine hydrochloride was found to be maintained 93%. Further, when shaked in the Clark Lubs buffer solution at 39° C. for 3 hours, L-lysine hydrochloride eluted 93%.

COMPARATIVE EXAMPLE 6

Without conducting the first coating treatment with hydroxypropyl cellulose in the step (b) in Example 23, the second coating treatment with 6,215 g of the slurry solution of Eudragit E100.aluminum.talc as used in the step (c) in Example 2 was applied directly to 800 g of the granules of from 9 to 10 mesh containing 71.8% of L-lysine hydrochloride obtained in the step (a) in Example 23. The coated product was dried to obtain 1,160 g of coated particles. The proportion of the coating layer obtained from the increase in the weight was 31.0%.

The particles thus obtained were subjected to shaking in the McDougall buffer solution at 39° C. for 24 hours, whereupon L-lysine hydrochloride was found to be maintained only 24.3%. Further, when shaked in the Clark Lubs buffer solution at 39° C. for 3 hours, L-lysine hydrochloride eluted 99.5%.

What is claimed is:

1. A feed additive for ruminants, which consists essentially of cores containing an acid salt of a basic amino acid, and effective amounts to attain the protection of the core material in a pH region corresponding to the rumen and to attain the release of the core material in a pH region corresponding to the abomasum of a first coating layer and a second coating layer coated sequentially on the surface of each core, wherein said first coating layer contains at least one first coating agent selected from the group consisting of a neutral or weakly acidic organic substance, a substantially neutral fine powder of inorganic substance, a non-ionic hydrophilic polymer substance and an anionic hydrophilic polymer substance and being physiologically acceptable to the ruminants, and the second coating layer contains as a second coating agent a polymer solube or swellable in water in an acidic region of a pH of at most 5.5.

2. The feed additive according to claim 1, wherein the first coating agent is a neutral or weakly acidic organic substance and/or a substantially neutral fine powder of inorganic substance.

3. The feed additive according to claim 2, wherein the fine powder of inorganic substance has a particle size of from 0.01 to 300 μm.

4. The feed additive according to claim 1, wherein the first coating agent is at least one organic substance selected from the group consisting of an amino acid, a natural nutrient, a protein and a carbohydrate.

5. The feed additive according to claim 4, wherein in the first coating layer, the first coating agent is in an amount of from 2 to 300 parts by weight per 100 parts by weight of the core.

6. The feed additive according to claim 1, wherein the first coating agent is at least one amino acid selected from the group consisting of methionine, leucine, isoleucine, valine, cysteine, tryptophan, threonine and phenylalanine.

7. The feed additive according to claim 1, wherein the first coating agent is at least one amino acid selected from the group consisting of methionine, leucine, isoleucine and tryptophan.

8. The feed additive according to claim 1, wherein the first coating agent is at least one fine powder of inorganic substance selected from the group consisting of talc, aluminum, muscovite, phlogopite, bentonite, silica, calcium silicate, kaolin, diatomaceous earth, magnesium silicate and aluminum silicate.

9. The feed additive according to claim 8, wherein in the first coating layer, the first coating agent is in an amount of from 2 to 200 parts by weight per 100 by weight of the core.

10. The feed additive according to claim 1, wherein the first coating agent is at least one fine inorganic substance selected from the group consisting of talc, silica, kaolin, magnesium silicate and aluminum silicate.

11. The feed additive according to claim 1, wherein the first coating agent is at least one non-ionic hydrophilic polymer substance selected from the group consisting of a synthetic polymer, a natural polysaccharide and a semisynthetic polymer substance.

12. The feed additive according to claim 11, wherein in the first coating layer, the first coating agent is in an amount of from 5 to 300 parts by weight per 100 parts by weight of the core.

13. The feed additive according to claim 1, wherein the first coating agent is at least one anionic hydrophilic polymer substance selected from the group consisting of a synthetic polymer substance and a semisynthetic polymer substance.

14. The feed additive according to claim 1, wherein the acid salt of a basic amino acid is a salt of at least one basic amino acid selected from the group consisting of lysine, arginine, histidine, hydroxylysine and ornithine, with at least one acid selected from the group consisting of hydrochloric acid, phosphoric acid, nitric acid and acetic acid.

15. The feed additive according to claim 1, wherein the cores comprise from 20 to 95% by weight of the acid salt of a basic amino acid, from 0 to 80% by weight of a biologically active substance other than the acid salt of a basic amino acid and from 2 to 50% by weight of a feed adjuvant.

16. The feed additive according to claim 15, wherein the biologically active substance is at least one member selected from the group consisting of a neutral amino acid, an amino acid derivative, a hydroxy homologue of an amino acid, a protein, a carbohydrate, a vitamin, and a veterinary medicine.

17. The feed additive according to claim 1, wherein the second coating agent is (a) a copolymer of dimethylaminoethyl methacrylate with an alkyl (meth)acrylate or (b) a copolymer of a vinylpyridine selected from the group consisting of 2-methyl 5-vinylpyridine, 2-vinylpyridine, 4-vinylpyridine, 2-vinyl-6-methylpyridine and 2-vinyl-5-ethylpyridine, with styrene or an acryl compound selected from the group consisting of an alkyl (meth)acrylate and acrylonitrile.

18. The feed additive according to claim 1, wherein in the second coating layer, the second coating agent is in an amount of from 10 to 200 parts by weight per 100 parts by weight of the core.

19. The feed additive according to claim 1, which is in the form of particles having a specific gravity of from 1.0 to 1.4.

20. The feed additive according to claim 1, wherein the ruminants are cattle, sheep or goat.

21. A feed additive according to claim 1, wherein cores contain an acid salt of a basic amino acid and a feed adjuvant, the first coating layer contains at least one first coating agent and supplementary additives, and the second coating layer contains a second coating agent and supplementary additives.

* * * * *